(12) United States Patent
Reneker et al.

(10) Patent No.: US 8,057,841 B2
(45) Date of Patent: Nov. 15, 2011

(54) MECHANICALLY ATTACHED MEDICAL DEVICE COATINGS

(75) Inventors: Darrell H. Reneker, Akron, OH (US); Daniel J. Smith, Stow, OH (US); Woraphon Kataphinan, Fontana, CA (US)

(73) Assignee: University of Akron, Akron, OH (US)

( * ) Notice: Subject to any disclaimer, the term of this patent is extended or adjusted under 35 U.S.C. 154(b) by 1009 days.

(21) Appl. No.: 10/597,899

(22) PCT Filed: Feb. 14, 2005

(86) PCT No.: PCT/US2005/004522
§ 371 (c)(1),
(2), (4) Date: Apr. 23, 2007

(87) PCT Pub. No.: WO2005/079335
PCT Pub. Date: Sep. 1, 2005

(65) Prior Publication Data
US 2008/0021545 A1    Jan. 24, 2008

Related U.S. Application Data

(60) Provisional application No. 60/544,010, filed on Feb. 12, 2004, provisional application No. 60/570,130, filed on May 11, 2004.

(51) Int. Cl.
*A61L 33/00* (2006.01)
(52) U.S. Cl. .......... 427/2.1; 623/1.15; 405/36; 210/503; 210/636; 210/650; 210/638; 606/29

(58) Field of Classification Search ................. 606/29; 623/1.15; 210/636, 503, 505; 405/36; 427/2.1
See application file for complete search history.

(56) References Cited

U.S. PATENT DOCUMENTS

| | | | |
|---|---|---|---|
| 4,983,068 A * | 1/1991 | Kozak et al. ............ | 405/36 |
| 5,376,117 A | 12/1994 | Pinchuk et al. | |
| 5,628,788 A | 5/1997 | Pinchuk | |
| 5,632,772 A | 5/1997 | Alcime et al. | |
| 5,639,278 A | 6/1997 | Dereume et al. | |
| 5,723,004 A | 3/1998 | Dereume et al. | |
| 5,855,598 A | 1/1999 | Pinchuk | |
| 5,948,018 A | 9/1999 | Dereume et al. | |
| 5,980,551 A | 11/1999 | Summers et al. | |
| 6,001,125 A | 12/1999 | Golds et al. | |
| 6,258,121 B1 | 7/2001 | Yang et al. | |
| 6,315,794 B1 | 11/2001 | Richter | |
| 6,569,195 B2 | 5/2003 | Yang et al. | |
| 6,627,246 B2 | 9/2003 | Mehta et al. | |
| 2002/0010505 A1 | 1/2002 | Richter | |
| 2002/0100725 A1* | 8/2002 | Lee et al. ............. | 210/503 |

(Continued)

FOREIGN PATENT DOCUMENTS
EP        1329230        7/2003
(Continued)

*Primary Examiner* — Dah-Wei Yuan
*Assistant Examiner* — Andrew Bowman
(74) *Attorney, Agent, or Firm* — Renner Kenner Greive Bobak Taylor & Weber

(57) ABSTRACT

The present invention relates to nanofibrous coatings on medical devices such a surgical mesh or stent, wherein the coating is mechanically attached to the device. The principal mechanism for attaching the coating is through causing the fibers to permeate and entangle with the substrate.

3 Claims, 5 Drawing Sheets

U.S. PATENT DOCUMENTS

| | | |
|---|---|---|
| 2003/0040790 A1 | 2/2003 | Furst |
| 2003/0088307 A1 | 5/2003 | Shulze et al. |
| 2003/0135255 A1 | 7/2003 | Sundar |
| 2003/0153901 A1 | 8/2003 | Herweck et al. |
| 2003/0190341 A1 | 10/2003 | Shalaby et al. |
| 2003/0195611 A1* | 10/2003 | Greenhalgh et al. ......... 623/1.15 |
| 2003/0211135 A1* | 11/2003 | Greenhalgh et al. .......... 424/443 |
| 2004/0073205 A1* | 4/2004 | Treat et al. ...................... 606/29 |
| 2004/0159609 A1* | 8/2004 | Chase ........................... 210/636 |

FOREIGN PATENT DOCUMENTS

| | | |
|---|---|---|
| WO | WO 02/49535 | 6/2002 |
| WO | WO 03/035134 | 5/2003 |
| WO | WO 03/082368 | 10/2003 |

* cited by examiner

MECHANICALLY ATTACHED MEDICAL DEVICE COATINGS

This application claims priority of U.S. Provisional Patent Application Ser. No. 60/544,010, which is herein incorporated by reference in its entirety.

BACKGROUND OF THE INVENTION

The present invention is directed to a medical device, such as a surgical mesh or stent, having a substrate and a fibrous coating. The fibrous coating is mechanically fixed to the substrate by entangling the fibers with pores, gaps, and/or through-holes located in the substrate. Entanglement is accomplished in a variety of ways including electrospinning nanofibers into a liquid that flows through the holes in the substrate in such a way that the fibers permeate the substrate and thereby mechanically attach thereto, thus forming a nanofiber sheet. The invention is particularly directed to nanofiber coatings, including nanofiber sheets.

A purpose of the nanofiber coating is to prevent adhesions between the mesh and internal organs. Attachment of the nanofiber sheets at the edges is not sufficient, because surgeons often cut the edges away to make the mesh fit the repair site. A typical mesh is made from a knitted sheet of polypropylene fibers, which are heat set so that the mesh retains its shape when subjected to shearing forces. Setting the mesh in this manner also enables it to withstand tensile forces, which is necessary to keep a hernia closed, for example. The coating generally needs to be present only on the side of the mesh that faces the internal organs that are to be protected from adhesions.

Some methods for attaching nanofibers to medical devices are known in the art. These include the use of glue to attach nanofiber sheets to the mesh, and attachment by suturing through the mesh. Unfortunately, using glue introduces additional substances into the body, which may have undesirable side effects. Suturing also presents problems in the sense that it is difficult to hold the nanofiber sheet in place while the mesh is being positioned during suturing. Other methods of coating medical devices with fibrous materials include, dipping, spraying, spin coating, electrospinning, and the nanofibers by gas jet (NGJ) method.

Greenhalgh et al. (U.S. Patent Application No. US 2003/0211135A1) discloses a stent device having an electrospun covering of a fibrous polymer layer. However, the layer is bonded to the device either by applying the polymer wet or by heating the polymer after being applied. In either case the attachment is through adhesion rather than entanglement of the fibers with the substrate.

As suggested above, prior work in the field of coated medical devices has employed a variety of means for attaching the coating to a substrate, but lacks any teaching of mechanically attaching fibrous layers by entangling them with the substrate. The present invention fills this gap in the art by providing several methods for attaching such coatings, and providing devices produced through the practice of these novel coating attachment methods.

SUMMARY OF THE INVENTION

The present invention is directed to a medical device, such as a surgical mesh or stent, having a substrate and a fibrous coating. The fibrous coating is mechanically attached to the substrate by entangling the fibers with pores, gaps, and/or through-holes located in the substrate. Entanglement is accomplished in a variety of ways including electrospinning nanofibers into a liquid that flows through the holes in the substrate in such a way that the fibers permeate the substrate and thereby mechanically attach thereto, thus forming a mechanically attached nanofiber coating.

The present invention is directed to a medical device comprising a porous substrate having openings therethrough, and a fibrous coating wherein at least one nanofiber is mechanically attached to said substrate through an opening in said substrate.

The present invention is further directed to a method for attaching a fibrous coating to a substrate comprising the step of pushing at least a portion of the fibrous coating through at least one hole in the surgical mesh.

The present invention is further directed to a method for attaching a fibrous coating to a substrate comprising the steps providing a substrate, coating a first side of the substrate with a fibrous coating, and forcing at least one fiber through an opening in the substrate.

The present invention is further directed to a means for mechanically bonding a fibrous coating to a substrate.

The following terms are specially defined. Entangle or entanglement, as used herein, refers to a mode of fiber attachment to a substrate that relies on frictional forces analogous to those which hold knotted string together. More particularly, fibers wrap or partially around the substrate and each other so that forces tending to lift the fibers from the substrate are counteracted by frictional forces between the fibers and the substrate.

BRIEF DESCRIPTION OF THJ DRAWINGS

DETAILED DESCRIPTION OF THE INVENTION

Figure 1:
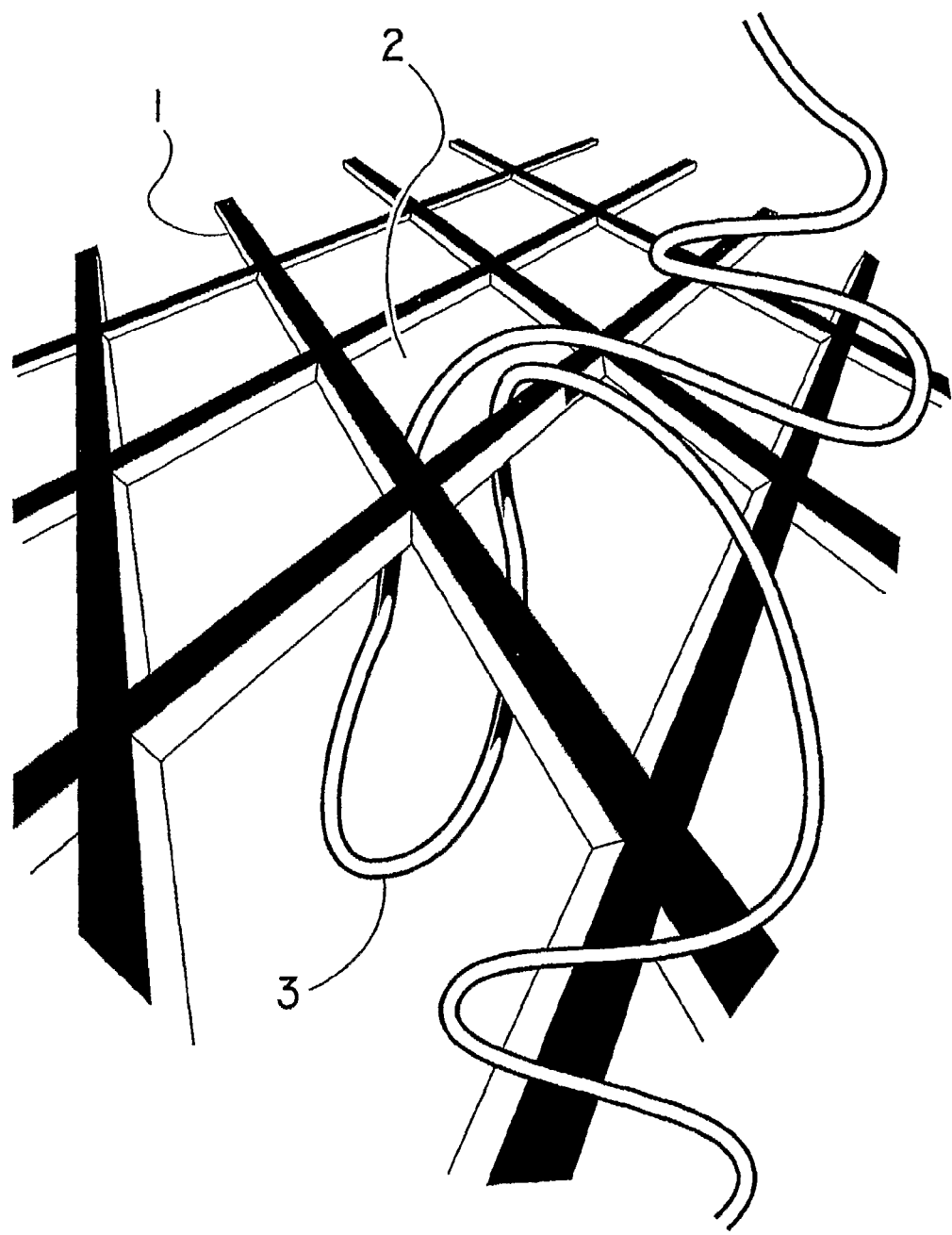
FIG. 1 is an illustration of a mesh, such as found in a medical device having nanofibers looped through the openings in the mesh.

The present invention is directed to medical devices such as surgical meshes and stents, which are implanted in the body. More particularly, the present invention is directed to coating such devices with nanofibers in a manner that results in the fibers being mechanically attached to the device.

In general a substrate within the scope of the present invention is a surface. More particularly, it is a surface having structures that may serve as mechanical attachment points. Such structures include holes, pores, gaps, fissures, through-holes, openings, orifices, foramen, fenestrae, bore and the like (hereinafter the foregoing are referred to collectively as "openings"). Any type of implantable medical device known in the art may be coated according to the present invention so long as it provides a suitably structured substrate. Surgical mesh and stents are particularly suitable due to their inherently net-like structure, which readily entangles with the fibers of the present invention. However, any device that is able to entangle with fibers or nanofibers to the extent that it results in a mechanical attachment. Typically, such devices comprise materials that allow fluids to permeate and pass through them, such as a fabric. Accordingly, various types of membranes, fabrics and gauzes may also form suitable substrates.

The fibers of the present invention are made from biocompatible materials, and are generally of a sufficiently small diameter to entangle with the openings in a substrate. Appropriate fibers are pliable to the extent that they may easily bend and form convoluted structures. Suitable materials for forming fibers of the present invention include, but are not limited to, polyolefins, polyethylene, polypropylene, linear poly(ethylenimine), cellulose acetate, and other preferably grafted cellulosics, poly(L-lactic acid), poly(caprolactone), poly (ethyleneoxide), poly(hydroxyethylmethacrylate), poly(glycolic acid) and poly vinylpyrrolidone.

Fibers of the present invention may be fabricated according to a variety of methods known in the art including electrospinning, wet spinning, dry spinning, melt spinning, and gel spinning. Electrospinning is particularly suitable for fabricating fibers of the present invention inasmuch as it tends to produce the thinnest (i.e. finest denier) fibers of any of the foregoing methods. Typically electrospun fibers can be produced having very small diameters, usually on the order of about 3 nanometers to about 3000 nanometers, and more preferably, on the order of about 10 nanometers to about 500 nanometers, and most preferably, on the order of about 10 nanometers to about 100 nanometers.

Another particularly effective method for producing nanofibers of the present invention comprises the nanofibers by gas jet method (i.e. NGJ method). This method has been previously described and is known in the art. Briefly, the method comprises using a device having an inner tube and a coaxial outer tube with a sidearm. The inner tube is recessed from the edge of the outer tube thus creating a thin film-forming region. Polymer melt is fed in through the sidearm and fills the empty space between the inner tube and the outer tube. The polymer melt continues to flow toward the effluent end of the inner tube until it contacts the effluent gas jet. The gas jet impinging on the melt surface creates a thin film of polymer melt, which travels to the effluent end of tube where it is ejected forming a turbulent cloud of nanofibers.

Electrospinning and NGJ techniques permit the processing of polymers from both organic and aqueous solvents. Furthermore, it has been discovered that dispersions of discrete particles and soluble non-fiber forming additives into the fluid to be spun into the fiber (i.e., the spin dope) does not prevent the formation of membranes using electrospinning and NGJ techniques. Therefore a wide variety of additives may be incorporated into fibers and devices of the present invention. Accordingly, medicinal additives may be included such as antimicrobial and antibiotic drugs, and various other therapeutic agents.

Fibers of the present invention may be spun directly onto the substrate and mechanically attached later. Alternatively, fibers of the present invention may be formed into free standing sheets, which are then applied to the substrate and mechanically attached. In another alternative, the fibers may be spun into a liquid or added to a liquid wherein they form a slurry, and the slurry may then be used to mechanically attach the fibers. Each of these options are discussed in detail below.

Figure 2:
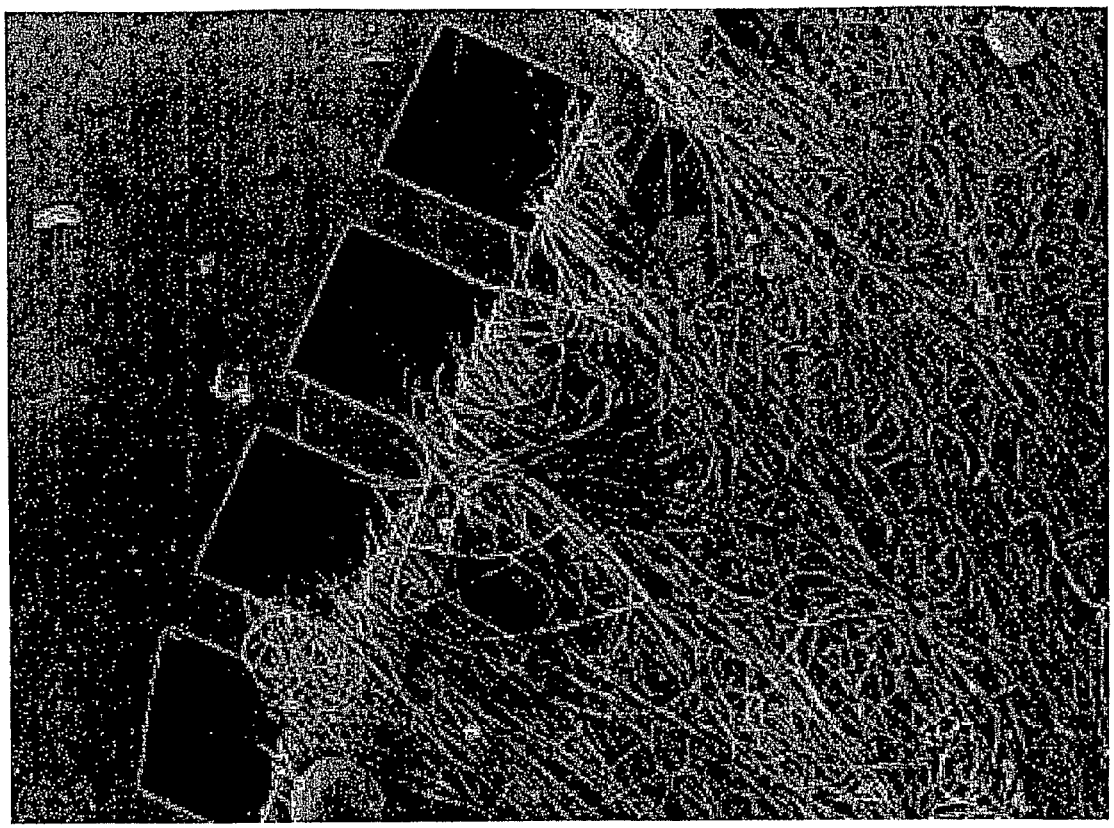
FIG. 2 is a photograph of nanofibers wrapping around and entangling with a substrate
Figure 3:
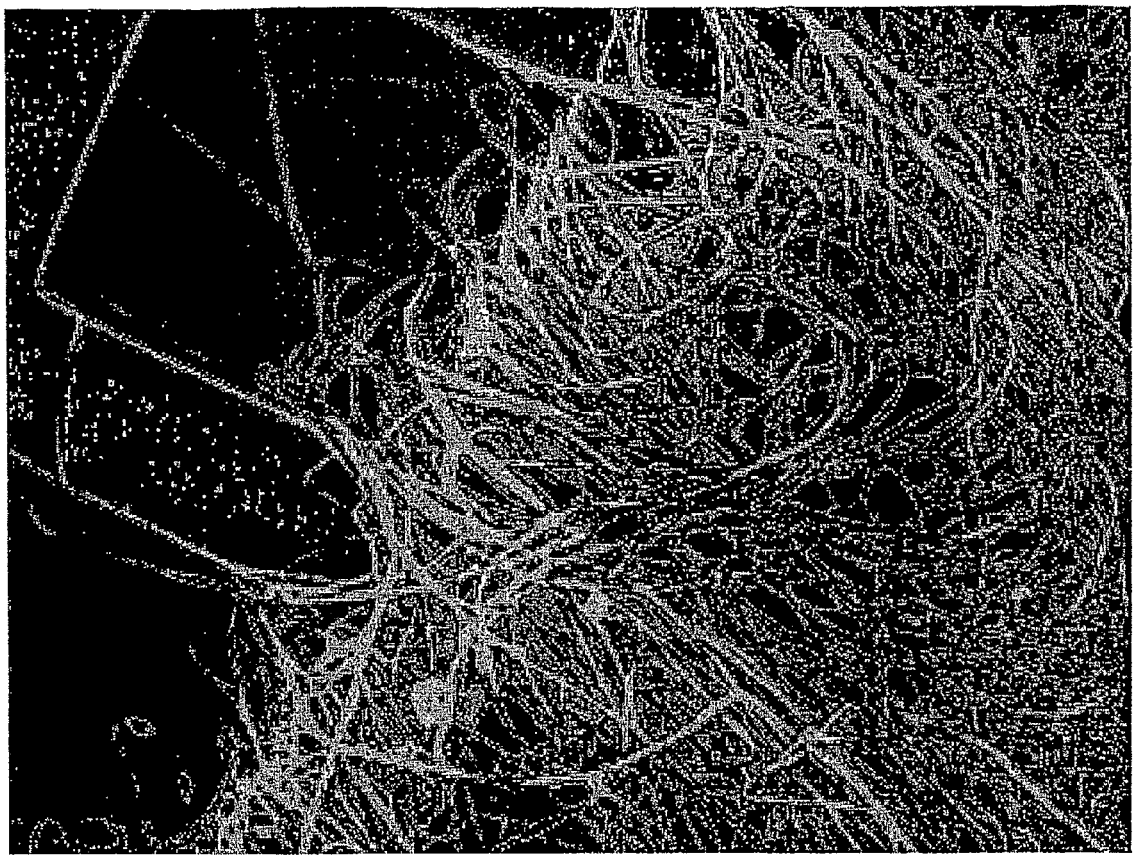
FIG. 3 is a close-up photograph of nanofibers wrapping around and entangling with a substrate
Figure 4:
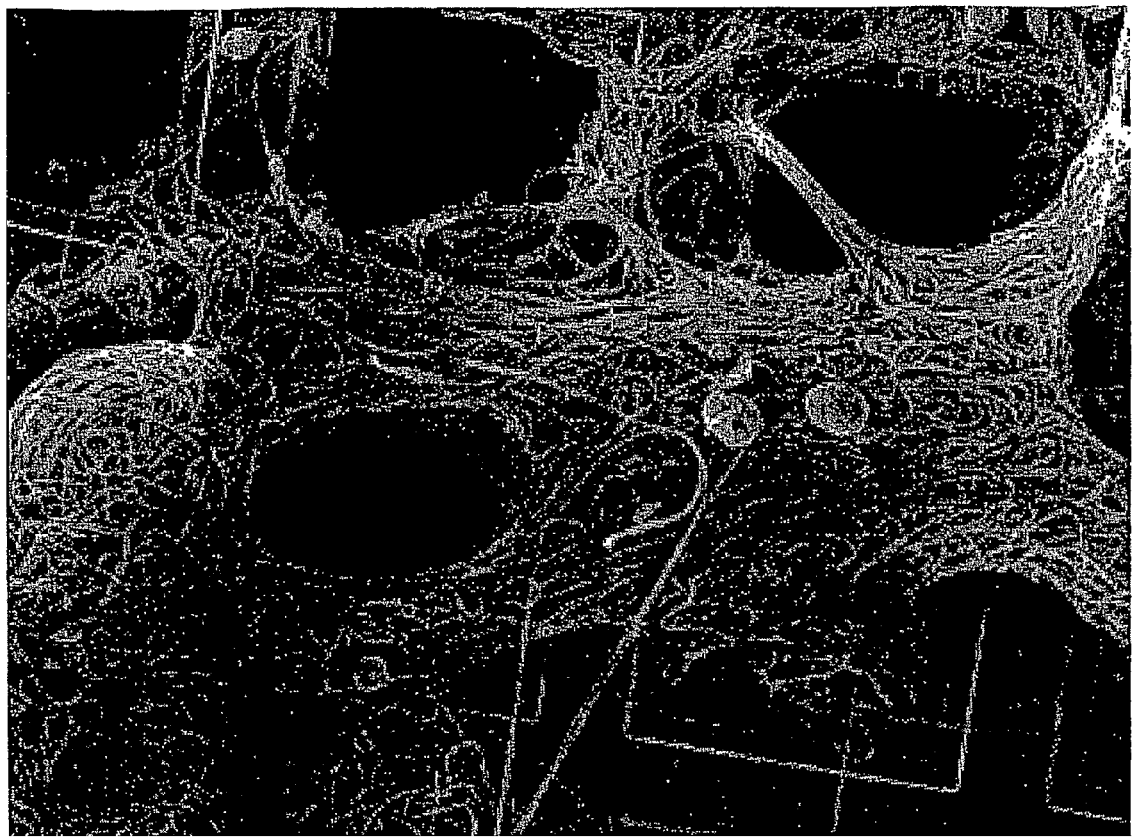
FIG. 4 is a close-up photograph of a hole in the nanofibrous coating caused by flowing fluid
Figure 5:
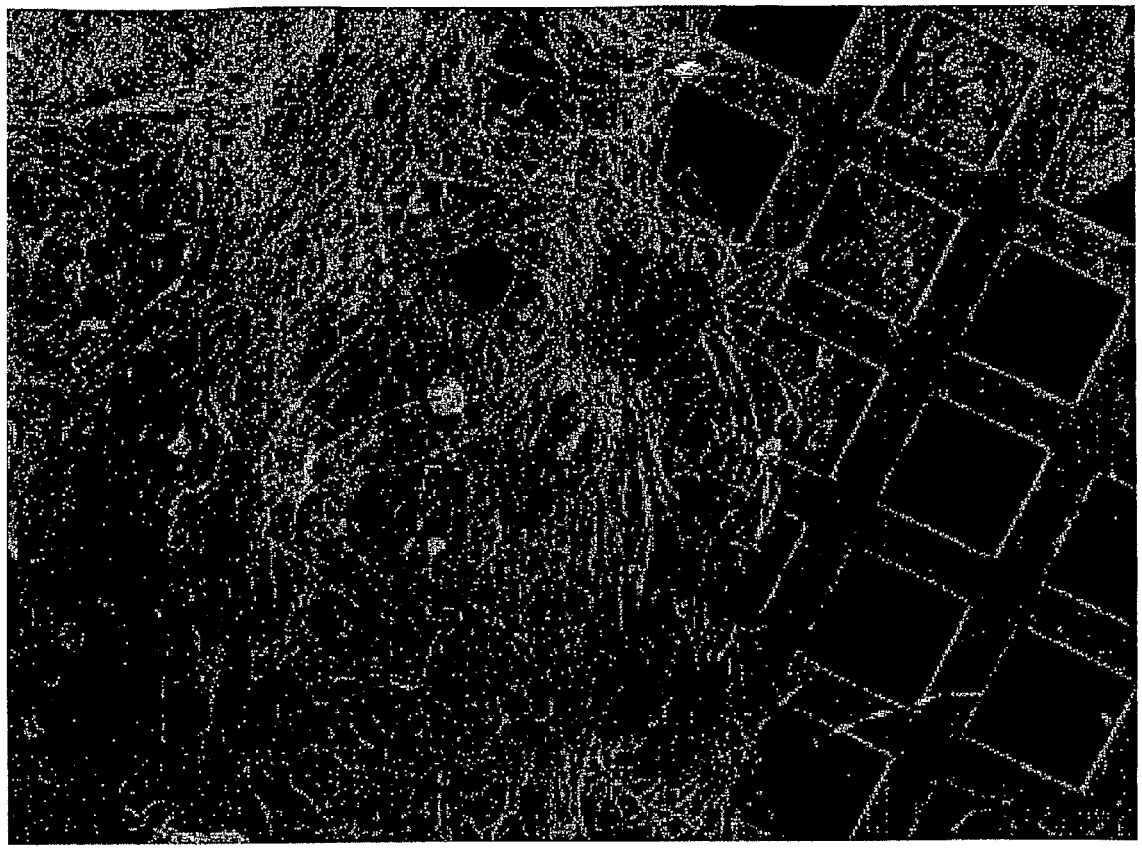
FIG. 5 is a photograph of a hole in the nanofibrous coating caused by flowing fluid

In general, methods for attaching fibers to substrates that are consistent with the present invention are methods that result in entanglement of the fibers with the substrate thus resulting in a mechanical attachment. FIG. 1 is an illustration showing generally how the mechanical attachment of the present invention operates. A fiber is shown to form a loop 3 that permeates a hole 1 in an arbitrary mesh-like object 2. The loop 3 wraps or partially wraps around a portion of the mesh 2 thus entangling with it. In such an arrangement, it is the frictional force between the fiber and the mesh 2 that forms the basis for the mechanical attachment. FIGS. 2 and 3 are photographs showing the same phenomenon diagramed in FIG. 1. In each figure an electron microscope grid serving as a substrate is shown entangled with nanofibers. For instance, FIG. 2 shows the nanofibers penetrating holes in the grid and wrapping around the elements forming the holes. FIG. 3 shows essentially the same thing, but shows a close-up of a single hole. Accordingly, a variety of methods are within the ambit of the present invention including without limitation (1) depositing fibers onto a substrate and using a barbed needle to pull fibers through one or more holes in the substrate, (2) working up the fibers into a slurry and forcing the slurry through the substrate thus causing the fibers to permeate the substrate, (3) applying fibers having opposite electric charges to opposing sides of the substrate and allowing the electric field to draw fibers through the holes, (4) depositing fibers onto a substrate and using pulses of fluid (e.g. gas or liquid) to force fibers through a hole or holes in the substrate, (5) melting or partially melting at least a portion of the fiber coating so that the melt flows around or partially around a portion of the substrate, thus mechanically bonding to the substrate, (6) using a substantially needle like object or array of such objects to push the fibers through holes in the substrate, and (7) adhering through self adhesion or adding adhesives.

A preferred method of effecting the fibers' mechanically attachment of the present invention comprises electrospinning the nanofiber into a fluid in which it is not soluble thus forming a slurry, and then causing the slurry to flow through the holes in the mesh. Both water and viscous solutions of water and sugar have been used to form useful loops in nanofibers. Fiber loops are carried through each of the holes in the mesh until the hole is filled with nanofibers. At this point, the thickness of the non-woven nanofiber sheet on the mesh is typically great enough to inhibit the formation of adhesions. If desired, a thicker sheet of nanofibers can be made, by collecting additional nanofibers that do not have loops passing through the holes.

If the nanofibers are collected on or in a viscous fluid, such as thick sugar syrup, for example, or viscous oil, loops of nanofibers can be carried through the holes in the mesh by very low velocity flow of the viscous fluid. The flow may be driven by atmospheric pressure forcing the fluid into a partial vacuum created on the downstream side of the mesh. Alternatively, the same effect can be achieved using a positive pressure to drive the fluid through the substrate. In either case the use of fluid to cause nanofibers to permeate and entangle with the substrate is a very effective method. The viscous fluid may be washed out of the coated mesh, or left in place if the fluid is benign or used to carry therapeutic substances.

Pulsating jets of fluid, often water, is another useful method of mechanically attaching. The water jet is ejected at a controlled pressure, just sufficient to force the nanofibers to deform and pass through the holes in the mesh. As the pressure is increased, some of the nanofiber loops forced through the holes may be broken, and the broken ends can form firm, conforming, attachments to the larger fibers in the mesh. At higher pressures, more of the nanofibers that pass through the holes will be broken and carried away. Choice of the optimal rate of erosion provides a method for attaching layers of nanofibers that are thicker than the diameter of the holes, by removing loops from the first layers in such a way that loops from the later layers can pass through the holes.

Control of the amount of solvent in the nanofiber when the nanofiber is collected can be used to allow the nanofiber to conform to the complicated contours of the mesh and adhere to the mesh without forming loops that actually pass through the holes in the mesh. Nanofibers that contain residual solvent can be made to "weld" together at crossing points to alter the mechanical properties of the non-woven structure, and to affect the removal rate of a bio-absorbable nanofiber, for example.

Some nanofibers, such as polyurethanes, are self-adherent, so that mechanically strong bonds form wherever nanofibers come into contact. Fibers with this contact-adhesive property can be held on the mesh if a thin layer of fibers is collected on the "outer" side of the mesh, and then forced into mechanical contact with the "working" nanofibers on the "in" side of the mesh by forces applied by an elastomeric roller for example. This provides a strong and uniform attachment of the nano fiber to the mesh when the nanofibers have "contact adhesiveness".

Immediate attachment of the nanofibers to the mesh during the spinning of the fibers provides support for the nanofibers and permits the use of a minimum thickness of the sheet of nanofibers, thereby minimizing the possibility of the nanofibers "pilling", or aggregating into other undesirable forms after implantation. Adherence of the nanofibers to each other, by contact adhesion, a deliberately applied adhesive, or by thermal adhesion, after the fiber sheet is deposited increases the mechanical stability of the sheet of nanofibers and avoids shifting of the nanofibers as an organ slides past the nanofiber coated mesh.

Thermal methods for attaching the polymer nanofibers to the mesh include:
1. Patterns created on a millimeter scale by localized melting of a sheet of nanofibers collected on the mesh. The "melted" pattern may or may not be correlated with the pattern of holes in the mesh. Not all pairs of polymers form adherent joints when their molten surfaces are brought into contact and solidified. For those pairs of polymers which do form adherent joints, this is a practical method that avoids any additional substances, since dry nanofibers can be collected into a non-woven sheet and then attached by the creation of a pattern of melted spots. The heating pattern can be established by a laser, for example a $CO_2$ laser beam directed by a computer controlled pattern generator. The advantages of the laser method of heating include the ability to form patterns with dimensions of from a few hundreds of microns to much larger patterns. It is straightforward with such a system to create patterns, which may be helpful in preventing adhesions, or other patterns, which can be read by eye or machine and used as labels, in addition to functioning as points of attachment between the nanofibers and the mesh.
2. The heating pattern can also be established by a hot "bed of nails", a pattern of hot wires, or other patterns engraved into a metal form that can be heated and pressed against the nanofiber sheet. This type of heating may be regarded as spot heating.
3. Localized melting produced by spot heating with a laser beam can produce controlled melting, controlled dissolution of certain areas, or controlled reactions if suitable liquids or gases are present. These altered areas may be useful for creation of surface patterns that inhibit the formation of adhesions.

If an array of electrically conducting needles protrudes through the holes in the mesh while the electrically charged nanofibers are being collected on the sheet, many of the nanofibers will be attracted to the points of the conducting needles. If the needles are withdrawn after the nanofibers are collected, many of the nanofibers will be pulled through the holes in the mesh. The segments of the nanofibers that are pulled through are attached to essentially all the layers of nanofibers collected. This mechanical method could be implemented by a roller or belt that carried needle-like "sprockets" that engaged a selected array of holes in the mesh just ahead of the area onto which the nanofibers are being deposited, and then disengaged as the mesh was transported forward, after a suitable layer of nanofibers was collected.

The electrospun nanofibers may carry either positive or negative excess charge. If a layer of positive nanofibers is applied to one side of the mesh and a layer of negative nanofibers is applied to the other side, the resulting electrical force is attractive and tends to cause the fibers to come together through the holes in the mesh. Optimizing this attractive force to bring the nanofibers into side-by-side contact, through the holes, provides yet another way to attach the nanofiber sheet to the mesh.

Thermal attachments were conducted with a $CO_2$ laser beam directed by a computer-controlled plotter. Hot pressing methods were successfully demonstrated by "heat sealing" nanofibers to polypropylene mesh. A hot bar type machine for sealing plastic bags was used. The width of the heated line was greater than appropriate for the millimeter scale mesh that is most desirable, but there are ways, described above, to make patterned heaters with desired scales. Several kinds of nanofibers can be attached to polypropylene mesh by heat-sealing "sandwiches" at the edges.

An embodiment of the present invention comprises a polypropylene surgical mesh coated on at least one side with a nanofibrous material. More particularly, the embodiment comprises a nanofibrous material that permeates openings in the mesh thus entangling with it. Such a mesh is suitable for repairing a hernia inasmuch as it prevents adhesions on the side facing internal organs. In another embodiment both sides of the mesh are coated with the same adhesion preventing nanofiber. In still another embodiment the two sides of the mesh are coated with different kinds of nanofibers. The first type is an adhesion preventative fiber, and the second type is an adhesion promoting fiber. Thus the mesh would tend to grow into the tissue facing away from the internal organs and thereby remain in place.

Medical devices of the present invention generally comprise any such device having a surface that is amenable to entangling with a fibrous material. Accordingly, such devices include without limitation bandages, gauzes, and stents. A gauze or bandage of the present invention may take the form of a non-stick bandage that tends not to adhere to or grow into a wound thus facilitating removal of the bandage. A stent made according to the present invention may incorporate adhesion-promoting fibers so that the stent tends to anchor itself in place by growing into the blood vessel.

The foregoing embodiments of the present invention have been presented for the purposes of illustration and description. These descriptions and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated. It is intended that the invention be defined by the following claims.

In order to demonstrate the practice of the present invention, the following examples have been prepared and tested.

The examples should not, however, be viewed as limiting the scope of the invention. The claims will serve to define the invention.

What is claimed is:

1. A method for attaching a fibrous coating to a substrate comprising the steps of:
   providing a substrate;
   coating a first side of the substrate with a fibrous coating; and
   forcing at least one fiber through an opening in the substrate,
wherein the fibrous coating includes fibers formed from one or more polyolefins, polyethylene, polypropylene, linear poly(ethylenimine), cellulose acetate, grafted cellulosics, poly(L-lactic acid), poly(caprolactone), poly(ethyleneoxide), poly(hydroxyethylmethacrylate), poly(glycolic acid) or polyvinylpyrrolidone,
wherein the step of forcing at least a portion of the fibrous coating through said opening in the substrate is performed by pulling a substantially needle-like object through said opening in the substrate, wherein a portion of the fibrous coating is pulled through said opening by the needle-like object.

2. A method for attaching a fibrous coating to a substrate comprising the steps of:
   providing a substrate;
   coating a first side of the substrate with a fibrous coating; and
   forcing at least one fiber through an opening in the substrate,
wherein the fibrous coating includes fibers formed from one or more polyolefins, polyethylene, polypropylene, linear poly(ethylenimine), cellulose acetate, grafted cellulosics, poly(L-lactic acid), poly(caprolactone), poly(ethyleneoxide), poly(hydroxyethylmethacrylate), poly(glycolic acid) or polyvinylpyrrolidone,
wherein the step of forcing at least a portion of the fibrous coating through said opening in the substrate is achieved by performing the additional steps of:
   inserting a portion of at least one substantially needle-like object through said opening;
   attaching at least one nanofiber to the substantially needle-like object; and
   withdrawing the substantially needle-like object from said opening so that the at least one nanofiber is pulled through said opening.

3. A method for attaching a fibrous coating to a substrate comprising the steps of:
   providing a substrate;
   coating a first side of the substrate with a fibrous coating; and
   forcing at least one fiber through an opening in the substrate,
wherein the fibrous coating includes fibers formed from one or more polyolefins, polyethylene, polypropylene, linear poly(ethylenimine), cellulose acetate, grafted cellulosics, poly(L-lactic acid), poly(caprolactone), poly(ethyleneoxide), poly(hydroxyethylmethacrylate), poly(glycolic acid) or polyvinylpyrrolidone;
applying a positively-charged fibrous coating to a first side of the substrate; and
applying a negatively-charged fibrous coating to a second side of the substrate.

* * * * *